(12) United States Patent
Ajiki et al.

(10) Patent No.: US 10,195,104 B2
(45) Date of Patent: Feb. 5, 2019

(54) GUM MASSAGING DEVICE AND METHOD FOR MASSAGING GUM

(71) Applicant: Panasonic Intellectual Property Management Co., Ltd., Osaka (JP)

(72) Inventors: Kaori Ajiki, Osaka (JP); Toshimitsu Minowa, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1042 days.

(21) Appl. No.: 14/597,280

(22) Filed: Jan. 15, 2015

(65) Prior Publication Data

US 2015/0216761 A1 Aug. 6, 2015

(30) Foreign Application Priority Data

Jan. 31, 2014 (JP) .................................. 2014-017121

(51) Int. Cl.
*A61H 13/00* (2006.01)
*A61H 23/02* (2006.01)
(Continued)

(52) U.S. Cl.
CPC ............. *A61H 13/00* (2013.01); *A61H 23/02* (2013.01); *A61H 2023/0227* (2013.01);
(Continued)

(58) Field of Classification Search
CPC .......... A61H 7/00–7/001; A61H 13/00; A61H 21/00; A61H 23/00; A61H 23/02;
(Continued)

(56) References Cited

U.S. PATENT DOCUMENTS 5,084,003 A   1/1992  Susic
5,667,487 A * 9/1997  Henley .................... A61N 1/30
                                                              604/20
(Continued)

FOREIGN PATENT DOCUMENTS

CN   1972729 A    5/2007
CN   201585617 U  9/2010
(Continued)

OTHER PUBLICATIONS

Satoshi Aihara et al., "Trend in Research on Organic Imaging Devices" NHK Science & Technology Research Laboratories R&D No. 132, pp. 4-11, Mar. 2012.
(Continued)

*Primary Examiner* — Rachel T Sippel
(74) *Attorney, Agent, or Firm* — Greenblum & Bernstein, P.L.C.

(57) ABSTRACT

A gum massaging device includes a sheet member closely attachable to a gum, a gum-condition sensor disposed on the sheet member, and a massaging element disposed on the sheet member at a position corresponding to a position at which the gum-condition sensor is disposed, the massaging element operating in accordance with a detection result from the gum-condition sensor. The gum-condition sensor detects, for example, a color tone of a portion of the gum adjacent to the gum-condition sensor. The massaging element provides, for example, a pinching massage to a portion of the gum adjacent to the massaging element.

6 Claims, 12 Drawing Sheets

(51) Int. Cl.
*A61N 1/20* (2006.01)
*A61N 1/26* (2006.01)

(52) U.S. Cl.
CPC .... *A61H 2201/10* (2013.01); *A61H 2201/165* (2013.01); *A61H 2201/5002* (2013.01); *A61H 2230/085* (2013.01); *A61H 2230/255* (2013.01); *A61H 2230/505* (2013.01); *A61H 2230/605* (2013.01); *A61N 1/205* (2013.01); *A61N 1/26* (2013.01)

(58) Field of Classification Search
CPC ........ A61H 23/0245; A61H 2023/0209; A61H 2023/0227; A61H 39/00; A61H 39/002; A61H 39/007–39/02; A61H 2201/10; A61H 2201/5002–2201/5005; A61H 2201/5058; A61H 2201/5082; A61H 2201/5089–2201/5094; A61H 2205/022; A61H 2209/00; A61H 2230/207–2230/208; A61H 2230/25–2230/255; A61H 2230/30–2230/305; A61H 2230/50
See application file for complete search history.

(56) References Cited

U.S. PATENT DOCUMENTS

| | | | |
|---|---|---|---|
| 2005/0256431 A1* | 11/2005 | Masuda | A61H 23/0245 601/2 |
| 2007/0224572 A1 | 9/2007 | Jon | |
| 2007/0257256 A1 | 11/2007 | Kugler | |
| 2009/0058274 A1 | 3/2009 | Yokoyama et al. | |
| 2010/0004715 A1* | 1/2010 | Fahey | A61H 39/002 607/48 |
| 2010/0305484 A1 | 12/2010 | Grollier et al. | |
| 2013/0323669 A1 | 12/2013 | Lowe | |

FOREIGN PATENT DOCUMENTS

| | | |
|---|---|---|
| CN | 102233156 A | 11/2011 |
| JP | 3-236289 | 10/1991 |
| JP | 2001-340412 | 12/2001 |
| JP | 2005-204869 A | 8/2005 |
| JP | 2007-300112 | 11/2007 |
| JP | 2008-237276 | 10/2008 |
| JP | 2009-048837 | 3/2009 |
| JP | 2011-024863 | 2/2011 |
| JP | 2011-505897 | 3/2011 |
| JP | 2012-125405 | 7/2012 |
| JP | 2013-168575 | 8/2013 |
| SU | 727194 | 4/1980 |
| WO | 2011/013533 | 2/2011 |

OTHER PUBLICATIONS

Takanori Kiyokura et al., "Wearable Laser Blood Flowmeter" NTT Technical Review, pp. 25-27, Nov. 2005.
The Extended European Search Report dated Jun. 29, 2015 for the related European Patent Application No. 15151584.8.
English Translation of Chinese Search Report dated Dec. 28, 2017 for the related Chinese Patent Application No. 201510032710.7.

* cited by examiner

FIG. 7

| BLOCK 611 | GUM-CONDITION SENSOR 612 | MASSAGING ELEMENT 613 | OPERATION PATTERN 614 |
|---|---|---|---|
| FIRST BLOCK | FIRST GUM-CONDITION SENSOR | FIRST TO FOURTH MASSAGING ELEMENTS | SEQUENTIALLY PROVIDE FIVE CYCLES OF MASSAGE CLOCKWISE |
| SECOND BLOCK | SECOND GUM-CONDITION SENSOR | FIFTH TO EIGHTH MASSAGING ELEMENTS | SEQUENTIALLY PROVIDE FIVE CYCLES OF MASSAGE CLOCKWISE |
| ..... | ..... | ..... | ..... |
| LTH BLOCK | MTH GUM-CONDITION SENSOR | ....TO NTH MASSAGING ELEMENTS | ... |

610

| GUM COLOR LEVEL | MASSAGE PATTERN | DETAIL OF MASSAGE PATTERN |
|---|---|---|
| NORMAL | I | PROVIDE NO MASSAGE OR ONE CYCLE OF MASSAGE |
| SLIGHT MUDDINESS | II | PROVIDE NORMAL MASSAGE (TWO CYCLES OF MASSAGE) |
| MUDDINESS | III | PROVIDE CAREFUL MASSAGE (THREE CYCLES OF MASSAGE) |
| DISCOLORATION | IV | PROVIDE STRONG MASSAGE (FIVE CYCLES OF MASSAGE) |
| LESION | V | PROVIDE NO MASSAGE |

GUM MASSAGING DEVICE AND METHOD FOR MASSAGING GUM

CROSS REFERENCES TO RELATED APPLICATIONS

This application claims priority to Japanese Patent Application No. 2014-017121, filed on Jan. 31, 2014, the contents of which are hereby incorporated by reference.

BACKGROUND

1. Technical Field

The present disclosure relates to a gum massaging device and a method for massaging a gum.

2. Description of the Related Art

Various devices for massaging the gums (referred to as "gum massaging devices", below) have been developed (see, for example, Japanese Unexamined Patent Application Publication No. 2011-24863 and Japanese Unexamined Patent Application Publication No. 2012-125405). A gum massaging device described in Japanese Unexamined Patent Application Publication No. 2011-24863 includes a tooth brush-like member through which an electric current is caused to pass. A gum massaging device described in Japanese Unexamined Patent Application Publication No. 2012-125405 includes a mouthpiece-like member, which covers the teeth and the gums and which is caused to vibrate.

The tooth brush-like member of the gum massaging device described in Japanese Unexamined Patent Application Publication No. 2011-24863 is applied to a portion of a user at which he/she wants to receive a massage. Alternatively, the mouthpiece-like member of the gum massaging device described in Japanese Unexamined Patent Application Publication No. 2012-125405 is put into the user's mouth. Thus, the technologies described in Japanese Unexamined Patent Application Publication No. 2011-24863 and Japanese Unexamined Patent Application Publication No. 2012-125405 (hereinafter referred to as "existing technologies") provide massages to the gums and improves the blood circulation of the gums.

However, the existing technologies are not suitable for effectively improving the conditions of the gums.

SUMMARY

One non-limiting and exemplary embodiment provides a gum massaging device capable of further effectively improving the conditions of the gums.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature a gum massaging device that includes a sheet member attachable to a gum, a gum-condition sensor disposed on the sheet member, and a massaging element disposed on the sheet member, the massaging element operating in accordance with a detection result from the gum-condition sensor.

The disclosed gum massaging device is capable of further effectively improving the conditions of the gums.

These general and specific aspects may be implemented using a system, a method, and a computer program, and any combination of systems, methods, and computer programs.

BRIEF DESCRIPTION OF THE DRAWINGS

FIG. 7 illustrates an example of a block information table according to the second embodiment;

DETAILED DESCRIPTION

Figure 1:
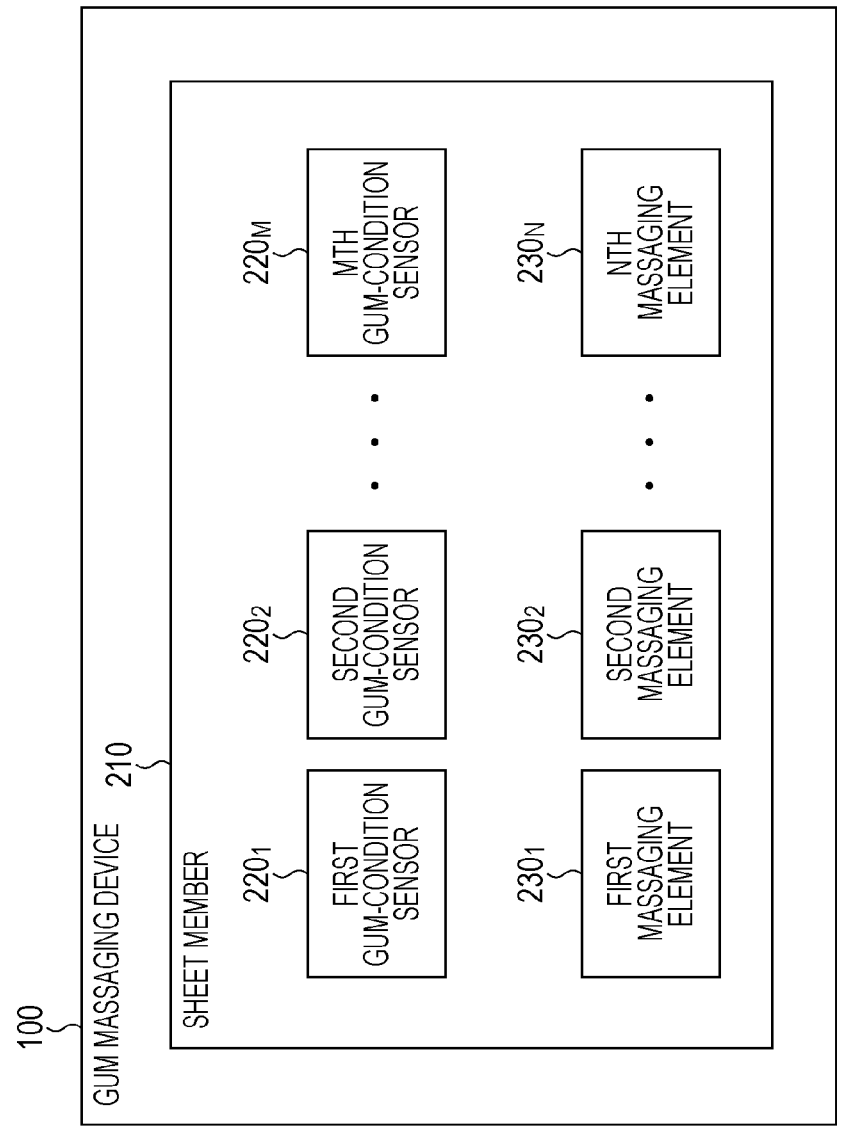
FIG. 1 illustrates an example of the configuration of a gum massaging device according to a first embodiment of the disclosure.

Knowledge Forming Basis of the Present Disclosure

The strength of a massage that a gum massaging device is to provide to the gum (the strength of a stimulus and the number of cycles of massage) differs depending on the conditions of the gums. For example, a portion having a poor blood circulation requires an active massage. On the other hand, providing an excessive massage to a portion having a good blood circulation should be avoided. Thus, to effectively improve the gum conditions each portion of the gums may receive a massage with an appropriate strength that is neither too low nor too high.

The gum conditions, however, are usually uneven and thus massaging the entirety of the gums with an appropriate strength is difficult. Moreover, even in the case where each portion is individually massaged, appropriately determining which portion of the gums is to receive a massage to what degree is difficult. In other words, existing technologies have difficulty in effectively improving the gum conditions.

Referring now to the drawings, embodiments of the disclosure are described in detail below.

First Embodiment

A first embodiment of the disclosure is an example of a basic form of the disclosure.

FIG. 1 illustrates an example of the configuration of a gum massaging device 100 according to this embodiment.

In FIG. 1, the gum massaging device 100 includes a sheet member 210, first to Mth (multiple) gum-condition sensors $220_1$ to $220_M$, and First to Nth (Multiple) Massaging elements $230_1$ to $230_N$.

The sheet member 210 is a member that can be closely attached to the gums.

The first to Mth gum-condition sensors $220_1$ to $220_M$ are disposed on the sheet member 210. Each of the first to Mth gum-condition sensors $220_1$ to $220_M$ detects the conditions of a portion of the gum adjacent to the gum-condition sensor.

The first to Nth massaging elements $230_1$ to $230_N$ are disposed on the sheet member 210 at positions corresponding to the positions at which the respective first to Mth gum-condition sensors $220_1$ to $220_M$ are disposed. Each of the first to Nth massaging elements $230_1$ to $230_N$ provides a massage to a portion of the gum adjacent to the massaging element. Each of the first to Nth massaging elements $230_1$ to $230_N$ operate in accordance with detection results from the one or more corresponding gum-condition sensors included in gum-condition sensors $220_1$ to $220_M$.

The gum massaging device 100 is capable of providing a massage to each portion of the gum to a degree appropriate for the conditions of the portion of the gum and thus capable of effectively improving the gum conditions.

The gum massaging device 100 may have one gum-condition sensor 220 on the sheet member 210 instead of multiple gum-condition sensors 220. The gum massaging device 100 may have one massaging element 230 instead of multiple massaging elements 230.

Second Embodiment

A second embodiment of the disclosure is an example of a specific form when the disclosure is applied to a member that can be fitted into an upper or lower oral vestibule (a space between the inner side of the cheeks and the corresponding gum).

Appearance and Configuration of Gum Massaging Device

Firstly, the appearance and the configuration of a gum massaging device 100 according to the embodiment will be described.

Appearance of Gum Massaging Device

Figure 2:
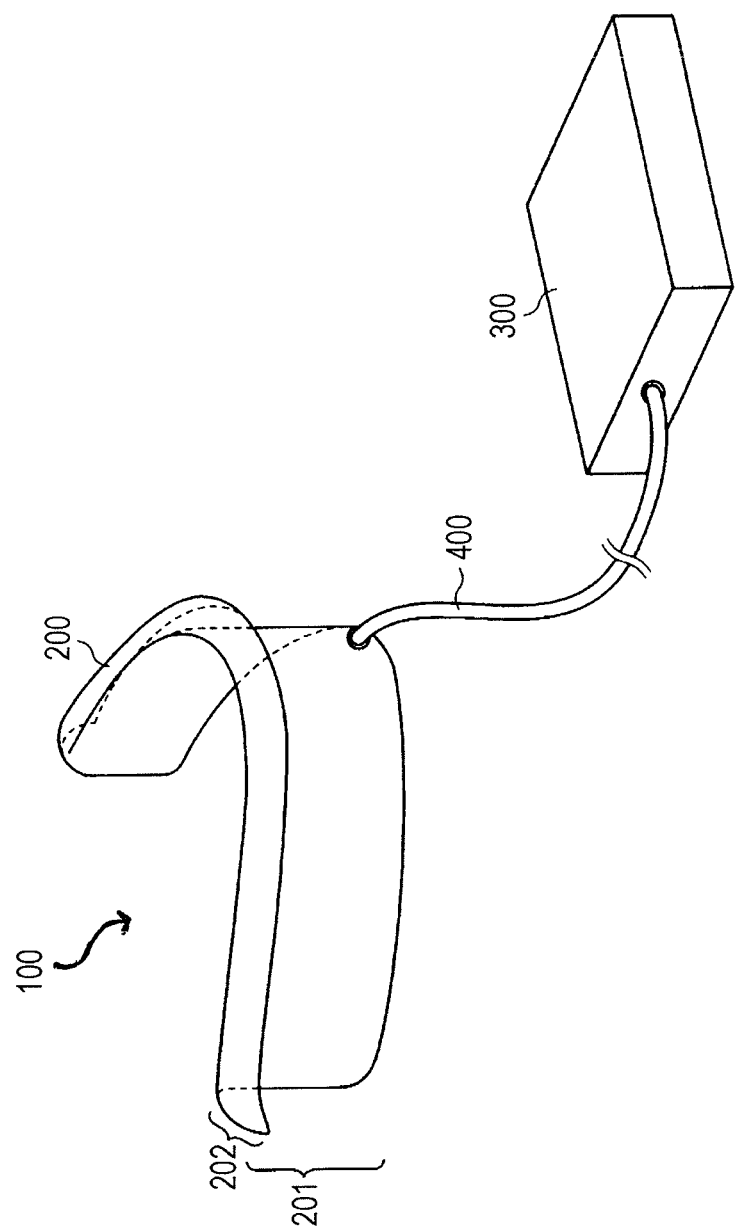
FIG. 2 illustrates an example of the appearance of a gum massaging device according to a second embodiment of the disclosure.

FIG. 2 illustrates the appearance of the gum massaging device 100 according to the embodiment.

As illustrated in FIG. 2, the gum massaging device 100 includes a sheet device 200 and a controlling unit 300.

The sheet device 200 is a sheet-like device having such a three-dimensional shape as to be fitted into an upper or lower oral vestibule.

The base material of the sheet device 200 is a sheet member having elasticity, flexibility, and resilience. At least part of the sheet device 200 is closely attached to the gum in the state where the sheet device 200 is fitted into the oral vestibule. More specifically, the sheet device 200 includes a body 201 and an edge portion 202 at the edge of the body 201. The body 201 is a portion that is closely attached to the gum. The edge portion 202 is a portion that is closely attached to a deep portion of the oral vestibule (a portion at the border between an inner side of the cheeks and the gum).

Figure 3:
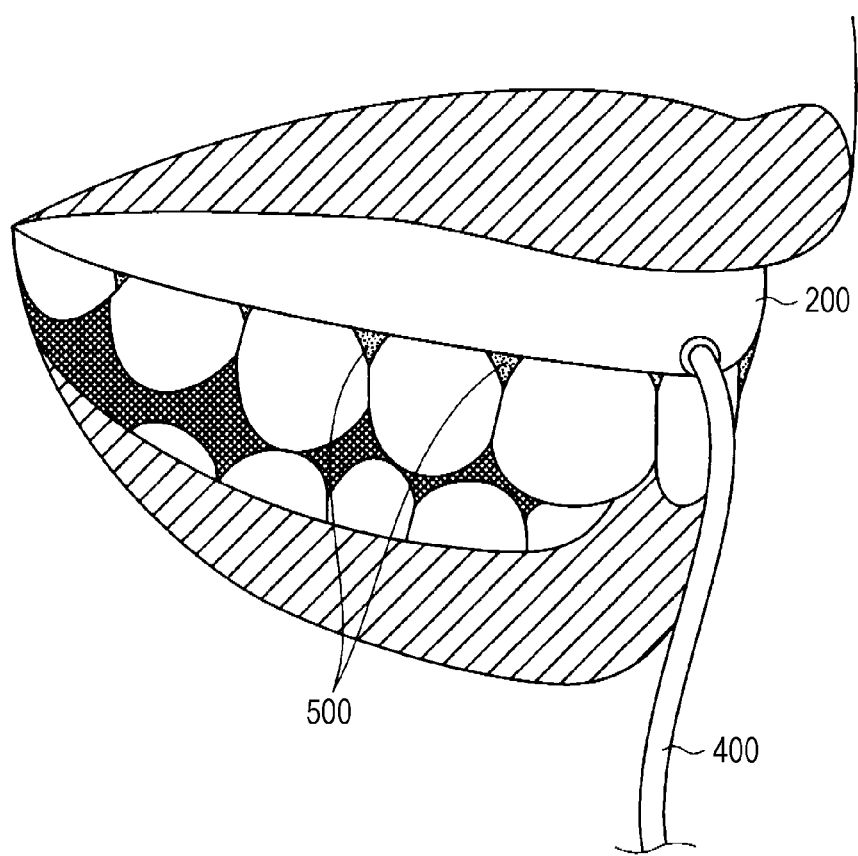
FIG. 3 illustrates an example of a sheet device according to the second embodiment that is in the used state.

FIG. 3 illustrates the state where the sheet device 200 is attached to the upper gum 500. If vertically inverted, the sheet device 200 is also attachable to the lower gum. The sheet device 200 is also attachable to the inner side of the gum (the side facing the tongue).

The body 201 of the sheet device 200 can keep closely attached to the gum 500 with the effects of the pressure from the inner side of the cheeks, the resilience of the sheet device 200, and the surface tension between the sheet device 200 and the gum. For securing sufficient adherence, a biocompatible adhesive such as spirit gum, a silicone adhesive, or a latex adhesive may additionally be used. The sheet device 200 could be selected from among multiple sizes and shape patterns in accordance with various sizes and shapes of the gum 500.

On the surface of the sheet member that is closely attached to the gum, multiple gum-condition sensors and multiple massaging elements (see FIG. 5) are disposed. The sheet member serves as the base member. The configuration of the sheet device 200 on which the multiple gum-condition sensors and the multiple massaging elements are arranged will be described in detail below.

Examples usable as the sheet member include a sheet member formed of a cured product of an energy-ray curable composition containing an acryloyl group-terminated urethane polymer and an acrylic monomer (see Japanese Unexamined Patent Application Publication No. 2013-168575).

The controlling unit 300 is a unit protected by a housing made of a material such as plastics. The controlling unit 300 has a function of controlling the operations of gum-condition sensors 220 and the massaging elements 230, which are described below. The controlling unit 300 is connected to the sheet device 200 with a cable 400.

Although not illustrated, the cable 400 includes signal lines that connect the controlling unit 300 to the gum-condition sensors 220 and the massaging elements 230. The cable 400 may have, for example, such a length that the controlling unit 300 can be held in a pocket of the user's cloth.

Unit by which Sheet Device is Controlled

In this embodiment, the operation of the sheet device 200 is controlled per section into which the sheet device 200 is divided, each section having sides of several millimeters to several centimeters. Hereinbelow, each section of the sheet device 200 or each unit by which the sheet device 200 is controlled is called a "block".

Figure 4:
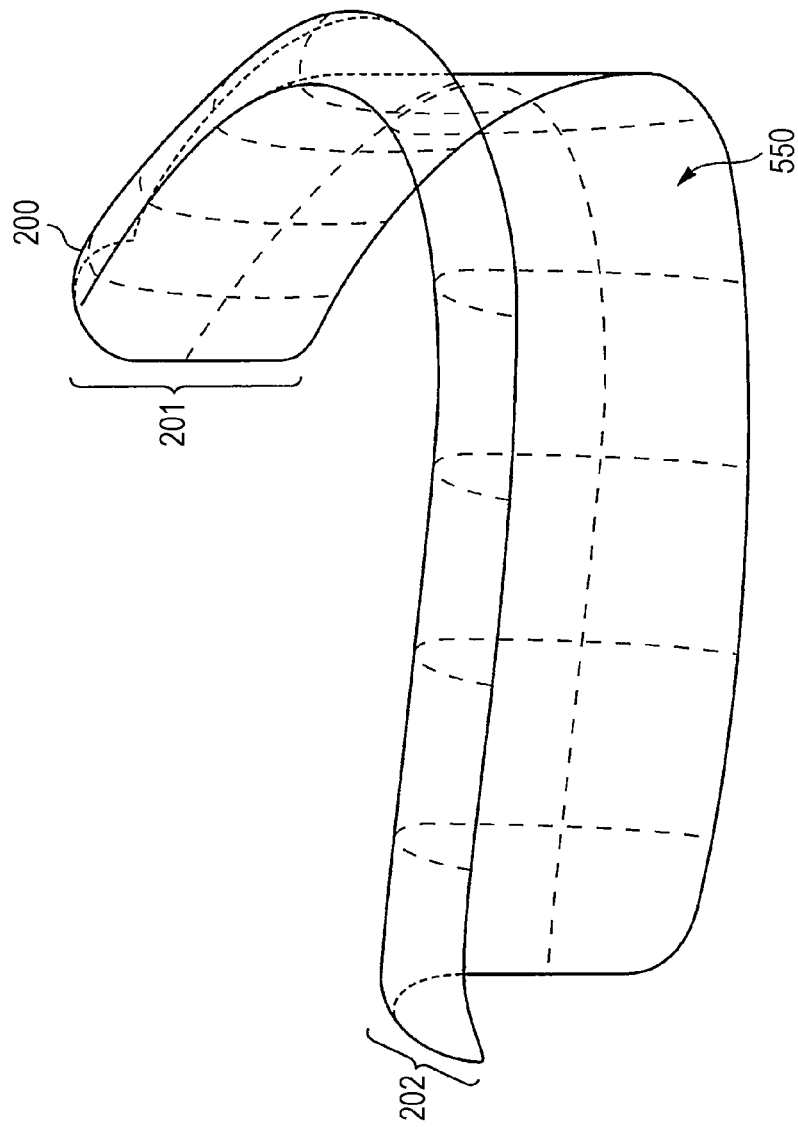
FIG. 4 illustrates an example of the arrangement of blocks according to the second embodiment.

FIG. 4 illustrates an example of the arrangement of blocks in the sheet device 200. FIG. 4 corresponds to FIG. 2.

As illustrated in FIG. 4, the sheet device 200 has multiple blocks 550 corresponding to sections into which the entire gum area is divided. The blocks 550 are sectional areas each obtained by equally dividing, for example, the sheet device 200 into ten sections in the lateral direction and into two sections in the longitudinal direction. The edge portion 202 may or may not be divided into blocks. Starting or stopping providing a massage or the strength of the massage can be individually controlled, for example, per block 550 in the sheet device 200.

In this embodiment, the sheet device 200 is assumed to have L blocks 550 having a substantially uniform area. In addition, one gum-condition sensor 220 and four massaging elements 230 are provided to each block 550.

Configuration of Sheet Device

Figure 5:
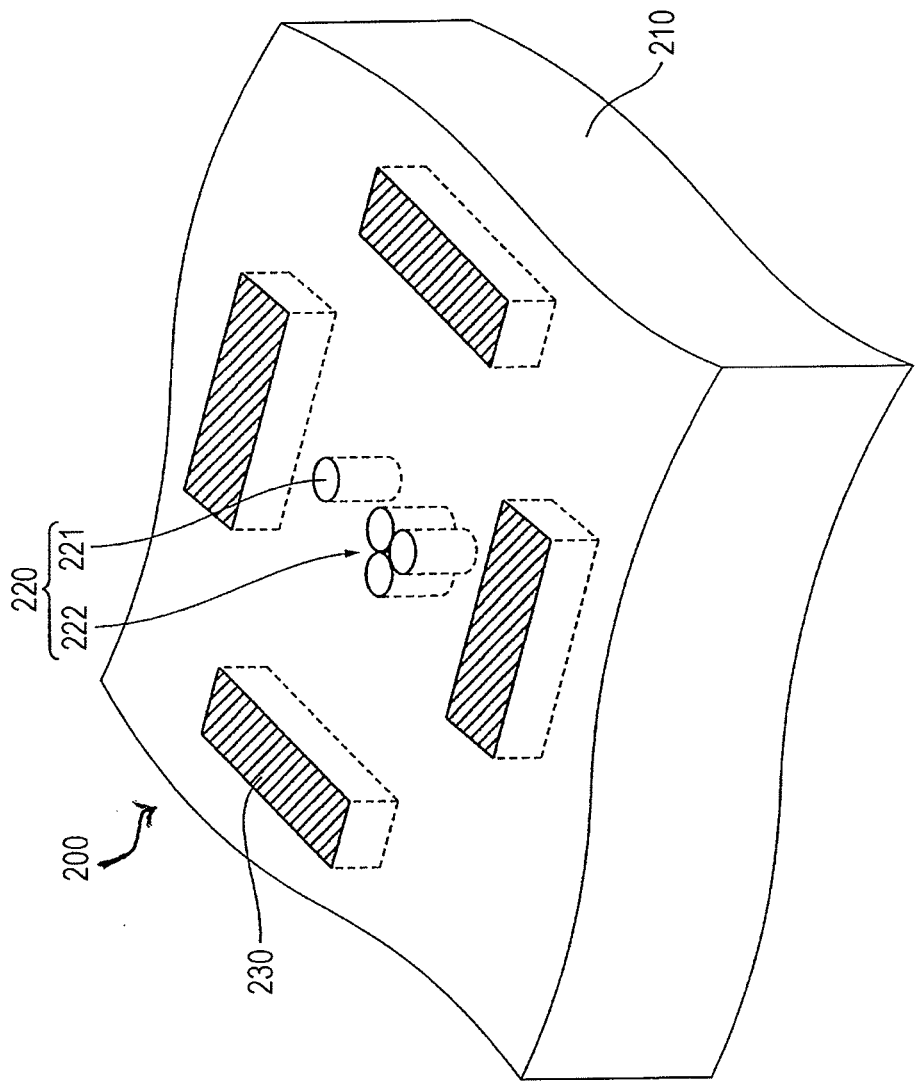
FIG. 5 illustrates an example of the configuration of the sheet device according to the second embodiment.

FIG. 5 illustrates an example of the configuration of the sheet device 200. FIG. 5 illustrates the main portion of the entire sheet device 200.

In FIG. 5, the sheet device 200 has a configuration in which a gum-condition sensor 220 and massaging elements 230 are embedded in the sheet member 210.

In this embodiment, as illustrated in FIG. 5, each block 550 has one gum-condition sensor 220 arranged at the center of the block 550 and four massaging elements 230 arranged so as to surround the gum-condition sensor 220. The blocks that are controlled are formed over the range including the body 201 and the edge portion 202 of the sheet device 200 (see FIG. 4).

The gum-condition sensor 220 detects the condition of a portion of the gum adjacent to the gum-condition sensor 220 in the state where the sheet device 200 is attached to the gum. The gum-condition sensor 220 detects the gum conditions including at least one of the color tone, the tension, the temperature, the blood pressure, the blood flow, and the water content of the gum.

In this embodiment, the gum-condition sensor 220 is a color tone sensor unit that detects the color tone of a portion of the gum adjacent to the sensor unit. The gum-condition sensor 220 serving as a color tone sensor unit includes, for example, a light-emitting device 221, which emits white light, and color tone sensors 222, which receive light that has been emitted by the light-emitting device 221 and reflected off the gum.

A light-emitting surface of the light-emitting device 221 and light-receiving surfaces of the color tone sensors 222 are exposed from the surface of the sheet member 210 that is closely attached to the gum (the upper surface in FIG. 5, hereinafter referred to as an "inner surface"). Preferably, the light-receiving surfaces of the color tone sensors 222 may be located inward from the inner surface of the sheet member 210. For example, the color tone sensor 222 is located so that the light receiving surface is positioned approximately 100 micrometers away from the gum in the state where the inner surface of the sheet member 210 is closely attached to the gum.

Examples usable as the light-emitting device 221 include an organic light emitting diode (LED) formed by printing using a polymer described in Japanese Unexamined Patent Application Publication No. 2009-48837. In addition, examples usable as the color tone sensors 222 include color tone sensors described in "Trend in Research on Organic Imaging Devices" written by Satoshi AIHARA and Misao KUBOTA, in NHK Science & Technology Research Laboratories R&D No. 132, issued by NHK Science & Technology Research Laboratories, in March 2012, pp. 4 to 11.

Each massaging element 230 provides at least one of a pinching massage and electrical stimulation to a portion of the gum adjacent to the massaging element 230 in the state where the sheet device 200 is attached to the gum. In this embodiment, each massaging element 230 serves as a massaging element that provides a pinching massage to the gum.

Here, the pinching massage is a massage for contracting the gum surface in the direction parallel to the gum surface. The contraction of the gum surface causes a pressure, which pushes the blood in the pressed portion of the gum aside to the surrounding portion of the gum. In short, the pinching massage is similar to a massage of lightly pressing the gum with fingertips.

The massaging elements 230 that provide a pinching massage may be formed using, for example, piezoelectric elements. Examples usable as the massaging elements 230 serving as piezoelectric elements include a piezoelectric element described in Japanese Unexamined Patent Application Publication No. 3-236289. In this case, operation surfaces of the massaging elements 230 are exposed from the inner surface of the sheet member 210. The massaging elements 230 provide a pinching massage in such a manner that a pair of adjacent massaging elements synchronously cause the gum to be contracted and shifted in accordance with the voltage. Here, a pair of piezoelectric elements that contract the gum may be regarded as one massaging element 230.

In this embodiment, the gum massaging device 100 sequentially provides a pinching massage from one portion to another portion over the gum surface in a predetermined direction. This operation similarly functions as a massage of putting and sliding fingertips over the gum.

Functional Configuration of Gum Massaging Device

Figure 6:
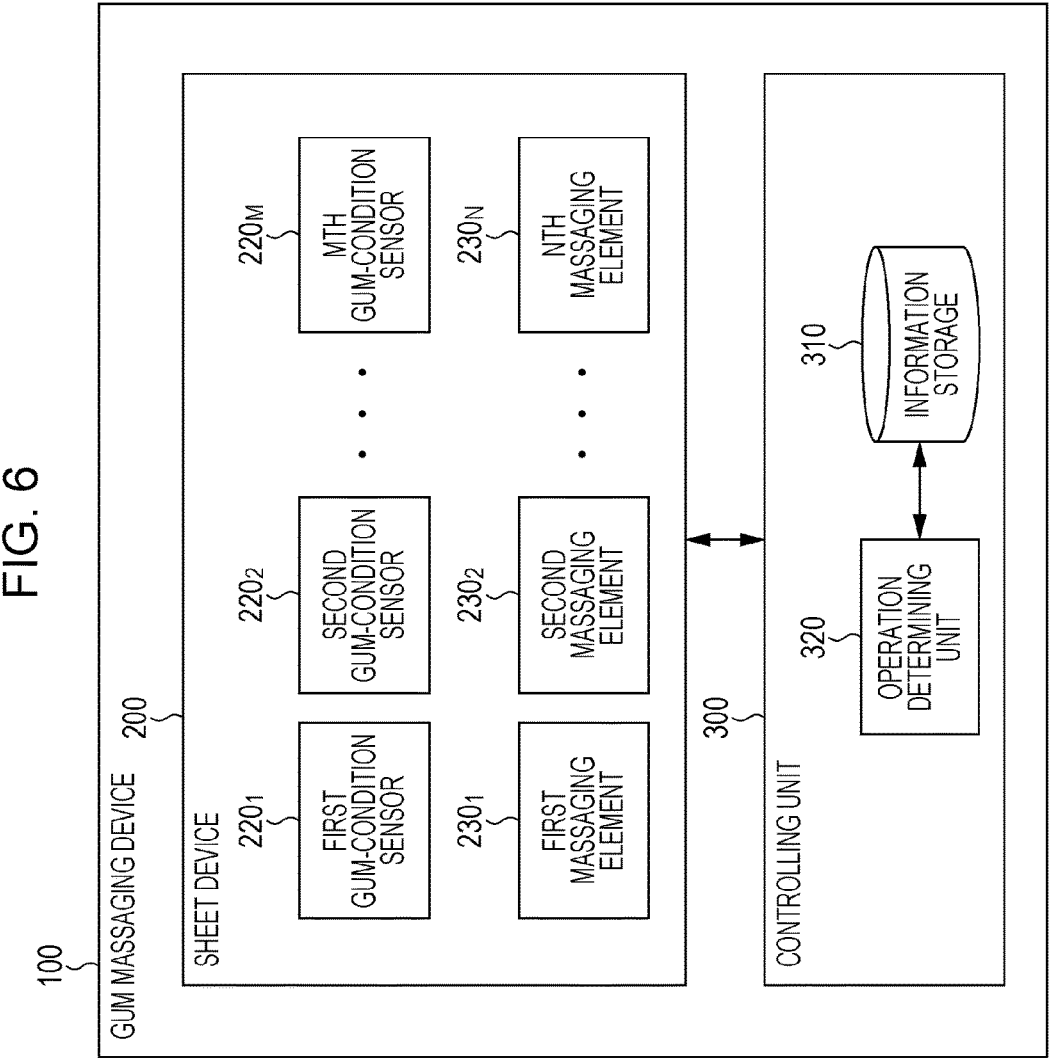
FIG. 6 illustrates an example of the functional configuration of a gum massaging device according to the second embodiment.

FIG. 6 illustrates an example of the functional configuration of the gum massaging device 100.

In FIG. 6, the gum massaging device 100 includes first to Mth gum-condition sensors $220_1$ to $220_M$ and first to Nth massaging elements $230_1$ to $230_N$, disposed in the sheet device 200, and an information storage 310 and an operation determining unit 320, disposed in the controlling unit 300.

The information storage 310 holds a block information table 610 and a control rule table 620 in advance. The block information table 610 is a table that specifies which gum-condition sensor 220 and which massaging element 230 are allocated to each block 550 and in which pattern the massaging element 230 is to be operated for massaging. The control rule table 620 is a table that specifies to what extent the gum massaging device 100 is to provide a massage in accordance with the gum conditions.

FIG. 7 illustrates an example of the block information table 610.

As illustrated in FIG. 7, the block information table 610 specifies, in association with an identification 611 of each block, an identification 612 of one gum-condition sensor 220 disposed in the corresponding block 550 and identifications 613 of four massaging elements 230. The block information table 610 also specifies, in association with the identification 611 of each block, a pattern in which the four corresponding massaging elements 230 are to be operated (hereinafter referred to as an "operation pattern").

For example, the area of the gum over which the first gum-condition sensor $220_1$ can detect the gum conditions and the area of the gum to which the first to fourth massaging elements $230_1$ to $230_4$, disposed around the first gum-condition sensor $220_1$, can provide a massage coincide with each other. Thus, controlling per block the operation of the corresponding massaging elements 230 on the basis of the detection results of the corresponding gum-condition sensor 220 enables massaging of the corresponding portion of the gum with a strength appropriate for the gum conditions of the portion.

Figure 8:
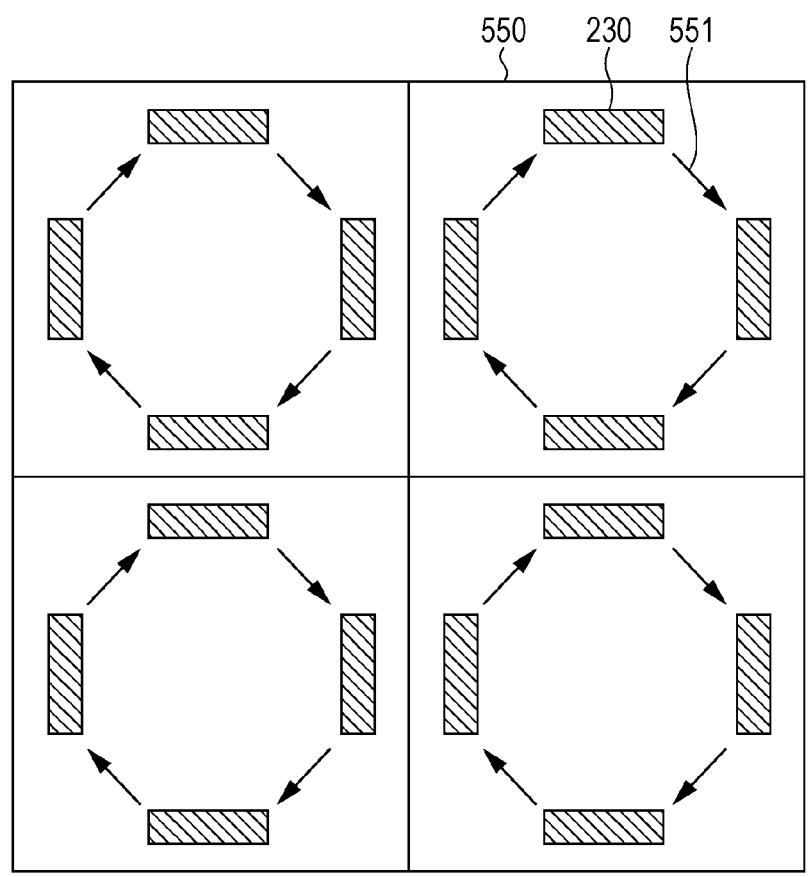
FIG. 8 illustrates an example of an operation pattern according to the second embodiment.

FIG. 8 illustrates an example of an operation pattern 614 (see FIG. 7) specified in the block information table 510. FIG. 8 illustrates an operation in four adjacent blocks 500.

The four massaging elements 230 disposed in each block 550 are sequentially switched from one to another clockwise to provide a pinching massage to the gum as indicated with arrows 551 in FIG. 8. The area of the gum to which each of the four massaging elements 230 provides a pinching massage (hereinafter referred to as a "massage area") shifts clockwise in each block. Such an operation pattern, such as the one in which the massaging elements 230 sequentially provide a pinching massage clockwise five cycles, is specified in the block information table 610.

Such a shift of the massage area similarly functions as a massage of, for example, putting fingertips on the gum and sliding the fingertips over the gum clockwise in a small area. Thus, the massaging device 100 can separately provide a massage to each block 550 by operating the corresponding massaging elements 230 in accordance with the block information table 610, thereby facilitating the blood circulation and improving the gum conditions.

The direction in which and the speed at which the massage area is shifted (that is, an operation pattern) may be the same throughout the blocks 550 or may differ between the blocks 550. The voltage applied to the massaging elements 230 during a pinching massage may be the same throughout the blocks 550 or may differ between the blocks 550 or between portions in each block 550.

In the following description, an operation of shifting the massage area within one block at a predetermined speed in accordance with the operation pattern 614 specified in the block information table 510 is defined as one massage operation unit (cycle).

Figure 9:
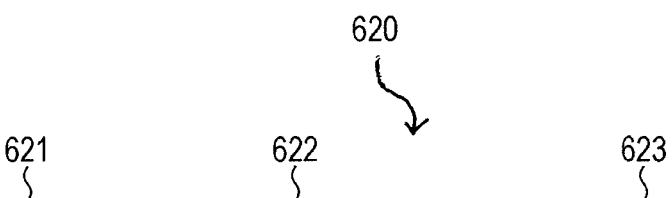
FIG. 9 illustrates an example of a control rule table according to the second embodiment.

FIG. 9 illustrates an example of the control rule table 620.

As illustrated in FIG. 9, the control rule table 620 specifies the identification 622 and the content 623 of the massage pattern in association with the gum color level 621.

The gum color level 621 is a category of the color tones of the gum in accordance with different blood flow levels. The massage pattern represents an operation pattern of the massaging element 230 associated with a massage with a predetermined strength. Specifically, the massage pattern is information that specifies how many cycles (including zero cycle) the block is operated.

For example, the gum color level 621 of "slight muddiness" is associated with the massage pattern identification 622 of "II" and the massage pattern content 623 of "normal massage (two cycles of massage)".

Such a massage pattern specifies, in an operation pattern 614 (see FIG. 7) specified in the block information table 610, that four massaging elements 230 allocated to a block 550 are operated two cycles. This massage pattern corresponds to a massage with a relatively low strength. This is because the blood circulation condition of the gum associated with the gum color level 621 of "slight muddiness" is relatively favorable and requires a light massage.

In addition, the gum color level 621 of "discoloration" is associated with the massage pattern identification 622 of "IV" and the massage pattern content 623 of "strong massage (five cycles of massage)".

Such a massage pattern specifies, in the operation pattern 614 (see FIG. 7) specified in the block information table 610, that four massaging elements 230 allocated to the block 550 are operated five cycles. This massage pattern corresponds to a massage with a relatively high strength. This is because the blood circulation condition of the gum associated with the gum color level 621 of "discoloration" is relatively unfavorable and requires a strong massage.

The gum color level 621 of "lesion" corresponds to the gum condition in which the gum should not receive a massage, as in the case where the gum has an inflammation. Thus, the gum color level 621 of "lesion" is associated with the massage pattern identification 622 of "V" and the massage pattern content 623 of "no massage". This is to prevent the gum condition from deteriorating with a massaging stimulus.

The control rule table 620 may be prepared for each block. Specifically, individual control rule tables 620 containing different contents may be prepared for different portions of the gum.

The operation determining unit 320 illustrated in FIG. 6 is connected to the first to Mth gum-condition sensors $220_1$ to $220_M$ and the first to Nth massaging elements $230_1$ to $230_N$ using a cable 400 (see FIG. 2), which connects the controlling unit 300 and the sheet device 200 together, and signal lines (not illustrated) embedded in the sheet device 200.

In other words, the operation determining unit 320 is capable of controlling the operations of the first to Mth gum-condition sensors $220_1$ to $220_M$ by transmitting control signals to the first to Mth gum-condition sensors $220_1$ to $220_M$ and capable of receiving detection values output from the first to Mth gum-condition sensors $220_1$ to $220_M$. The operation determining unit 320 is also capable of controlling the operations of the first to Nth massaging elements $230_1$ to $230_N$ by transmitting control signals to the first to Nth massaging elements $230_1$ to $230_N$.

The operation determining unit 320 acquires the gum condition (gum color level) corresponding to each block 550 on the basis of the detection results (gum color tone) input from the corresponding gum-condition sensor 220. The operation determining unit 320 then refers to the block information table 610 (see FIG. 7) and the control rule table 620 (see FIG. 9) and determines the operations of the massaging elements 230 on the basis of the acquired gum conditions.

Specifically, the operation determining unit 320 determines the operations of the massaging elements 230 so that the block 550 corresponding to a portion of the gum having a lower blood circulation provides a massage with a higher strength.

Although not illustrated, the controlling unit 300 includes, for example, a central processing unit (CPU), a storage medium such as a read only memory (ROM) in which a control program is stored, and an operation memory such as a random access memory (RAM). In this case, the function of each portion of the controlling unit 300 is implemented by the CPU executing the control program.

Although not illustrated, the controlling unit 300 includes a power source unit and an operation unit such as a key switch. The power source unit supplies power to operate the CPU and the sheet device 200. The operation unit receives various instructions including an instruction of starting a massage from a user.

The gum massaging device 100 having such a configuration is capable of providing a massage with a strength appropriate for the condition of each portion of the gum.

Operation of Gum Massaging Device

Now, the operation of the gum massaging device 100 is described.

Figure 10:
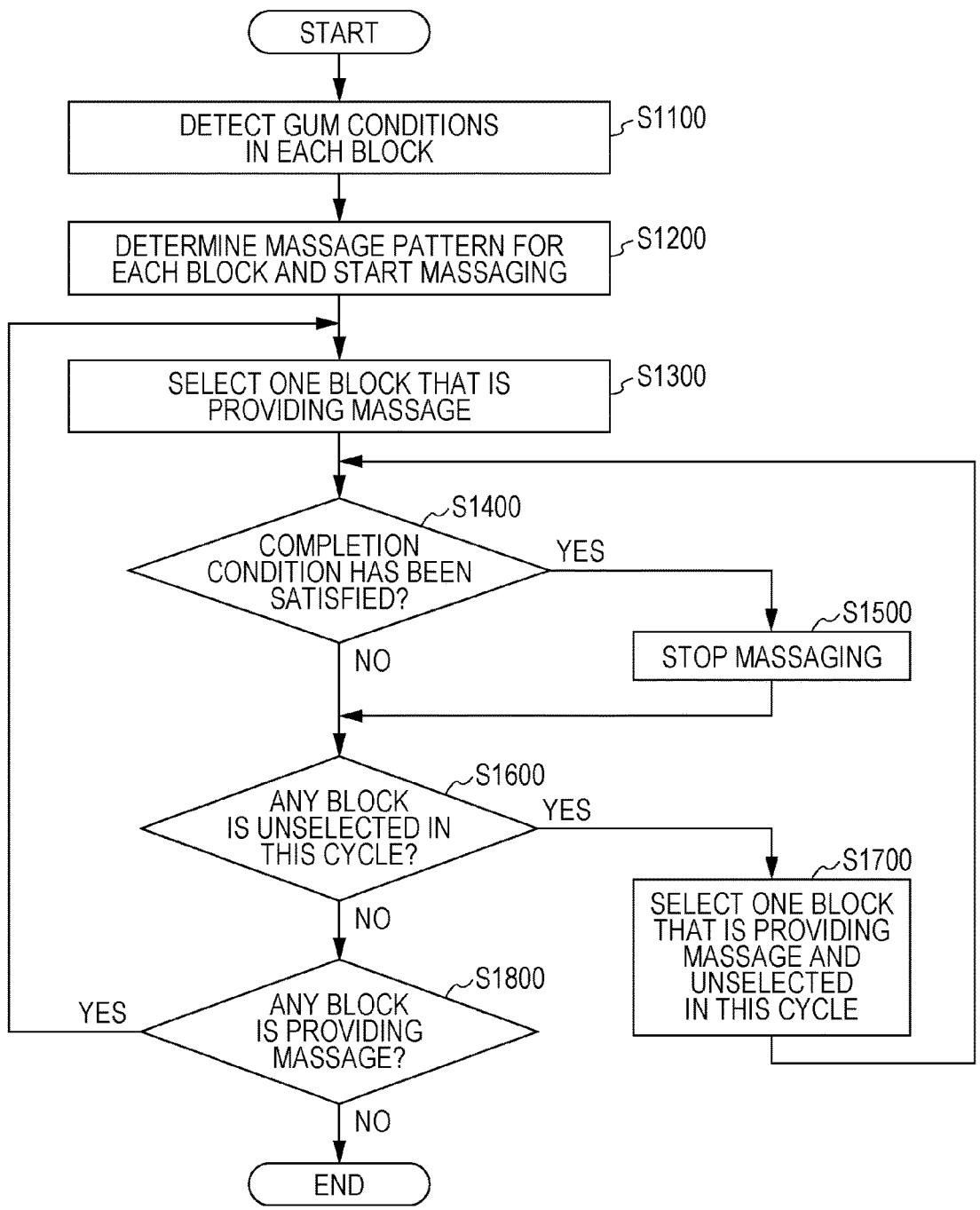
FIG. 10 is a flowchart illustrating an example of the operation of the gum massaging device according to the second embodiment.

FIG. 10 is a flowchart illustrating an example of the operation of the gum massaging device 100.

The gum massaging device 100 starts the following processing when a user instructs the gum massaging device 100 to start the operation in the state where the sheet device 200 is attached to the user's gum.

In Step S1100, the first to Mth gum-condition sensors $220_1$ to $220_M$ detect the gum conditions (color tone) before providing a massage and output the detection results to the operation determining unit 320. The operation determining unit 320 determines the gum color level for each gum-condition sensor 220 on the basis of the input detection result from the corresponding gum-condition sensor 220. To determine the gum color level, the operation determining unit 320 refers to, for example, the table that is stored in the information storage 310 in advance and in which the gum color tone and the gum color level are associated with each other.

In Step S1200, the operation determining unit 320 determines a massage pattern for each block 550 on the basis of an initial detection value for the block 550. Then, the massaging elements 230 in each block 550 are started to operate in the corresponding operation pattern 614 (see FIG. 7).

In Step S1300, the operation determining unit 320 selects one of blocks 550 that are providing a massage. The operation determining unit 320 handles a process up to a transition of operations after Step S1800, which is described below, as one processing cycle. This cycle is a concept different from one cycle of the above-described operation pattern.

In Step S1400, the operation determining unit 320 determines whether the selected block 550 has satisfied a completion condition.

The completion condition here represents that a massage specified by the massage pattern determined in Step 1200 has been finished. For example, in the case where a massage pattern content of "normal massage (two cycles of massage)" is determined, the completion condition is that two cycles of the corresponding operation pattern have been finished.

In the case where the completion condition of the selected block 550 is satisfied (YES in S1400), the processing of the operation determining unit 320 proceeds to Step S1500. In the case where the completion condition of the selected block 550 is not satisfied (NO in S1400), the processing of the operation determining unit 320 proceeds to Step S1600.

Here, the case where the completion condition is not satisfied is the state where the massage has not yet been completely provided, whereas the case where the completion condition is satisfied is the state where the massage has been fully provided but has not yet become excessive.

In Step S1500, the operation determining unit 320 stops the selected block 550 from providing the massage and the processing of the operation determining unit 320 proceeds to Step S1600.

In Step S1600, the operation determining unit 320 determines whether there is any block 550 that is providing a massage and that has not been selected in this cycle. In the case where there is any block 550 that is providing a massage and that has not been selected (YES in S1600), the processing of the operation determining unit 320 proceeds to Step S1700. In the case where there is no block 550 that is providing a massage and that has not been selected (NO in S1600), the processing of the operation determining unit 320 proceeds to Step S1800.

In Step S1700, the operation determining unit 320 selects one of the blocks 550 that are providing a massage and that have not been selected and the processing returns to Step S1400.

In Step S1800, the operation determining unit 320 determines whether there is any block 550 that is providing a massage. When there is any block 550 that is providing a massage (YES in S1800), the processing of the operation determining unit 320 returns to Step S1300. When there is no block 550 that is providing a massage (NO in S1800), the processing of the operation determining unit 320 is finished.

In this manner, the massaging device 100 is capable of providing a massage, block by block, for an appropriate length of time (number of cycles) corresponding to the gum condition.

Effects of Gum Massaging Device

As described above, the gum massaging device 100 according to the embodiment is capable of providing a massage with an appropriate strength to a portion of the gum that requires a massage, such as a portion having a poor blood circulation, without the user having to determine to which portion of the gum and how strong a massage is to be provided.

Thus, the gum massaging device 100 according to the embodiment is capable of enhancing the conditions of the entire gum in balance while a massage is prevented from becoming excessive even when the conditions of the entire gum vary from portion to portion. In short, the gum massaging device 100 according to the embodiment is capable of effectively improving the gum conditions.

The gum massaging device 100 according to the embodiment is also capable of massaging the gum without the user holding the device with his/her hands. Thus, the user can use the gum massaging device 100 while performing other operations. Furthermore, the use of the massaging device 100 according to the embodiment can prevent, for example, a massage from being biased in favor of the portion of the gum on the dominant-hand side.

Other Examples of Operation Pattern

The operation pattern of the massaging elements 230 is not limited to the example described above. In addition to the operation pattern illustrated in FIG. 8, the massaging device 100 may provide a massage, for example, in an operation pattern in which the massage area is rotationally shifted within a larger range.

Figure 11:
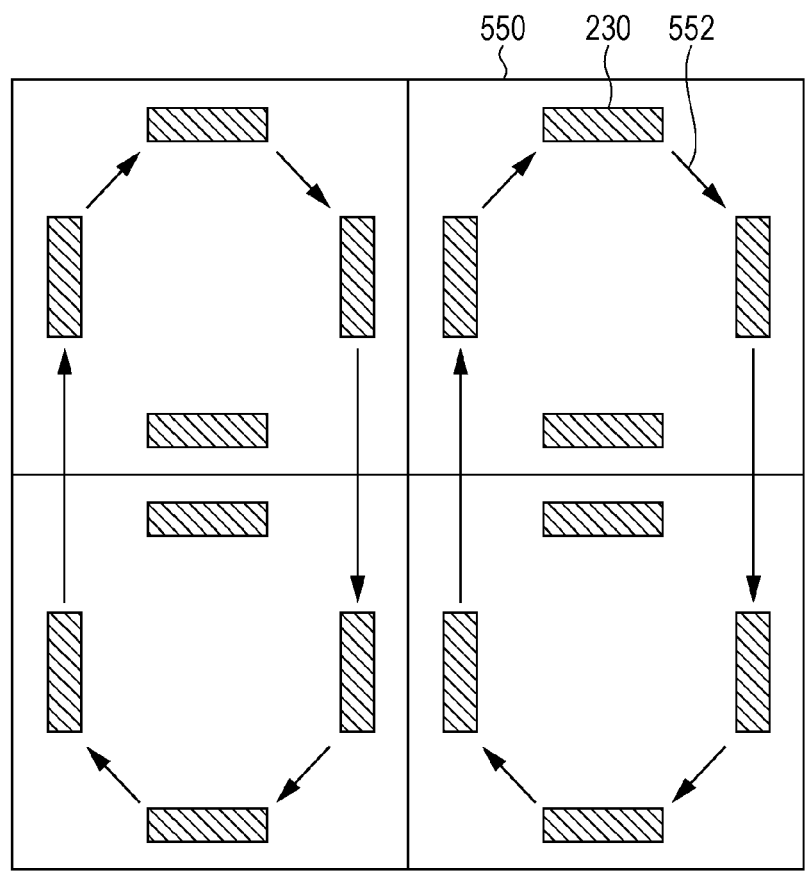
FIG. 11 illustrates another example of the operation pattern according to the second embodiment.

FIG. 11 illustrates another example of the operation pattern. FIG. 11 corresponds to FIG. 8.

In the operation pattern illustrated in FIG. 11, the massage areas are sequentially switched from one to another clockwise, as indicated with arrows 552, among six massaging elements 230 located on the outer periphery of two vertically adjacent blocks 500.

Such a shift of the massage area similarly functions as, for example, a massage in which fingertips slide over the gum clockwise in a large area while pinching the gum.

Such a massage over a large area may be provided to, for example, an area including the gum and a junction between the gum and the inner side of the cheeks (specifically, corresponding to an area stretching over the body 201 and the edge portion 202 of the sheet device 200). In this case, the blood flow can be enhanced between the gum and the inner side of the cheeks.

The direction in which, the order in which, the speed at which, and the way how the massage areas are sequentially switched from one to another, the way how the massaging elements 230 are arranged, and other conditions are not limited to the examples illustrated in FIG. 8 and FIG. 11. For example, the gum massaging device 100 may have massaging elements 230 arranged in a matrix and may alternate the area at which the corresponding massaging element 230 provides a pinching massage between adjacent areas in a checkered-pattern manner.

The arrangement of the blocks 550, the blocks 550 that are to be controlled, and the arrangement or the number of the gum-condition sensors 220 and the massaging elements 230 in each block are not limited to the examples described above.

Example that Includes Salivary-Gland Massaging Function

The salivary glands are situated in the back of the oral vestibule. The salivary glands having a poor blood circulation may fail in normal salivation. Thus, the gum massaging device 100 may also have a salivary-gland massaging function in addition to a gum massaging function.

Figure 12:
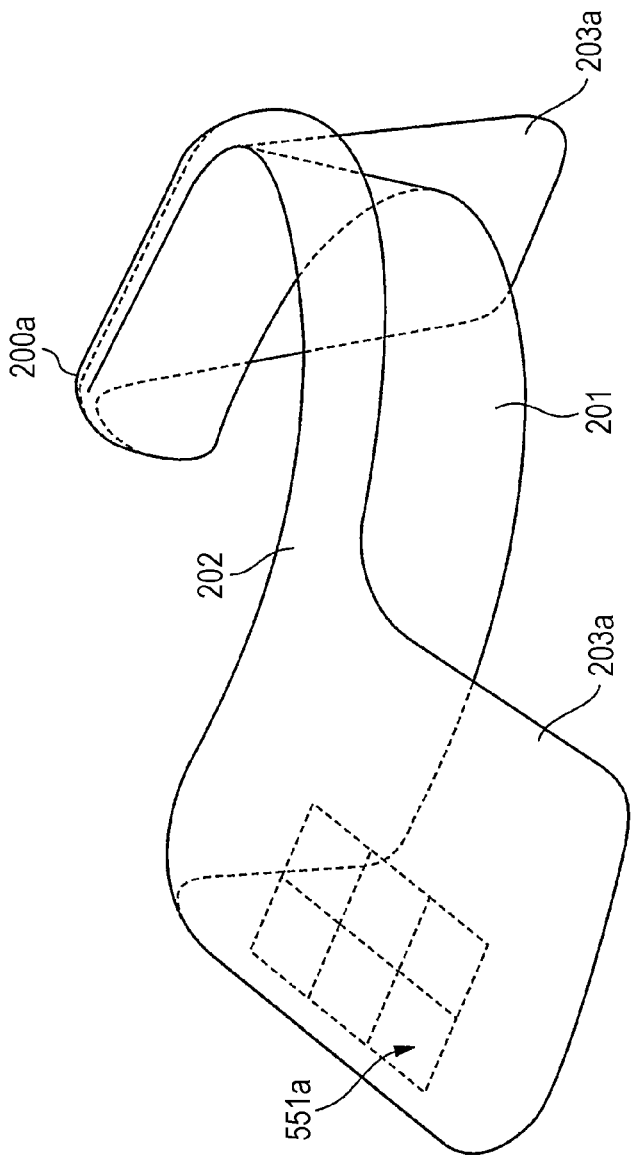
FIG. 12 illustrates another example of the appearance of the gum massaging device according to the second embodiment.

FIG. 12 illustrates an example of the appearance of a gum massaging device including a salivary-gland massaging function. FIG. 12 corresponds to FIG. 2. FIG. 12 illustrates a sheet device 200a.

As illustrated in FIG. 12, a sheet device 200a includes, for example, two wing portions 203a extending leftward and rightward from the edge portion 202. Each wing portion 203a comes into contact with a mucous membrane near the corresponding salivary gland at the back of the oral vestibule in the state where the sheet device 200a is attached to the gum.

At a portion of each wing portion 203a corresponding to the salivary gland, one or more blocks 551a for massaging the salivary gland (hereinafter referred to as "salivary-gland massaging block/blocks") are disposed. In each salivary-gland massaging block 551a, at least one massaging element 230 (salivary-gland massaging element) is disposed. In this case, the operation determining unit 320 controls the operation of the salivary-gland massaging blocks independently of other blocks 550 (see FIG. 4).

As in the case of other blocks 550, for example, one gum-condition sensor 220 and four massaging elements 230 are disposed in each salivary-gland massaging block 551a. In this case, the gum-condition sensor 220 detects the color tone of the mucous membrane on the inner side of the cheek. The operation determining unit 320 determines the operation of the massaging elements 230 in each salivary gland block 551a on the basis of the color tone of the mucous membrane detected by the corresponding gum-condition sensor 220. The operation determining unit 320 may determine the same operation for the massaging elements 230 in adjacent salivary gland blocks 551a.

Example Including Sterilization Function

The gum massaging device 100 may also have a function of sterilizing the oral cavity.

In this case, the gum massaging device 100 includes an electrically stimulating portion. The electrically stimulating portion applies a voltage of 1.5 V to the oral cavity to cause a weak current of approximately 2 mA to pass through the oral cavity through saliva in the state, for example, where the sheet device 200 is attached to the gum. Such passing of a current enables sterilization of the gum and other portions in the oral cavity using saliva.

Passing of a current from the electrically stimulating portion may affect the operations of the gum-condition sensor 220 and the massaging elements 230. To prevent this effect, the gum massaging device 100 may operate the electrically stimulating portion, for example, after the completion of providing a massage.

Example of Using Relative Value of Color Tone

The gum massaging device 100 may determine the operation of each massaging element 230 on the basis of a relative value of the color tone, not an absolute value of the color tone. Specifically, the operation determining unit 320 compares the color tones detected in multiple blocks and determines that a stronger massage is to be provided to a portion having a poorer blood circulation than other portions. Thus, massages can be provided in consideration of differences in gum color between individuals.

Use of Other Gum Information

The massaging device 100 may determine the operation of each massaging element 230 on the basis of various types of information related to the gun-condition detected from the gum by the gum-condition sensor 220, the information representing the necessity of a massage other than the color tone. Examples of the gum-condition-related information representing the necessity of a massage include the tension, the temperature, the blood pressure, the blood flow, and the water content of the gum. The strength of a massage that is to be provided to the gum in accordance with each detected value may be determined through, for example, experience and experiment.

Examples usable as the gum-condition sensor 220 that includes a blood flow sensor to detect the blood flow include a blood flow sensor described in "Wearable Laser Blood Flowmeter" written by Takanori KIYOKURA, Shinji MINO, and Junichi SHIMADA in NTT Technical Review November 2005, issued by Nippon Telegram and Telephone Corporation (NTT Microsystem Integration Laboratories), pp. 25 to 27. The blood flow sensor includes a laser diode and a phototransistor. Examples usable as the laser diode include an organic laser diode formed by printing using a polymer described in Japanese Unexamined Patent Application Publication No. 2009-48837. Examples usable as the phototransistor include an organic phototransistor formed by a polymeric thin film transistor described in Japanese Unexamined Patent Application Publication No. 2007-300112.

The massaging device 100 may determine the operation of each massaging element 230 on the basis of a combination of various types of information representing the gum conditions.

Other Modified Examples

The degree to which the gum conditions change in response to massages with the same strength varies between individuals. The massaging element 230 may thus stop providing a massage when the degree to which the corresponding gum condition (for example, the color tone) has changed from the start of the massage arrives at a predetermined threshold. This configuration can prevent provision of an excessive massage regardless of the individual differences.

The sheet device 200 may be sized smaller or larger than the one illustrated in FIG. 3. The control unit 300 may be connected to a sheet device 200 attached to an upper gum and a sheet device 200 attached to a lower gum.

In the case where the sheet device 200 is highly water resistant, the user can use the gum massaging device 100 while holding water in his/her oral cavity. This configuration can prevent the temperature of the oral cavity from rising excessively high as a result of the massage provided by the massaging elements 230.

Part or the entirety of the functions of the control unit 300 according to the above-described second embodiment may be included in an apparatus that has another function as a main purpose such as a mobile phone.

The above-described functions may be implemented by a network server. Specifically, the function of a portion of the gum massaging device 100 may be implemented by cloud computing. In this case, the operation determining unit needs to include at least a communication unit so as to transmit data of the gum condition to the server and obtain the time at which the massage is to be stopped.

The gum massaging device 100 may include, in each block, an operation determining unit 320 that performs operations for the corresponding block. In this case, the operation determining unit 320 may be, for example, a comparator that compares a signal output from the gum-condition sensor 220 with a predetermined threshold and outputs the comparison result as a control signal for the massaging element 230.

The gum has a so-called "trigger point". Thus, the gum massaging device 100 may provide a massage with the block located at such a trigger point. Then, changes in blood flow that occur after the massage may be measured by the sheet device 200 or another sheet device attached to a portion other than the gum to estimate the user's health.

A gum massaging device disclosed herein includes a sheet member attachable to a gum, a gum-condition sensor disposed on the sheet member, and a massaging element disposed on the sheet member, the massaging element operating in accordance with a detection result from the gum-condition sensor.

In the disclosed gum massaging device, the gum-condition sensor may detect information related to a condition of the gum, the condition including at least one of a color tone, a tension, a temperature, a blood pressure, a blood flow, and a water content. The massaging element may provide a massage to the gum, the massage including at least one of a pinching massage and electrical stimulation.

The disclosed gum massaging device may include a plurality of gum-condition sensors that includes the gum-condition sensor disposed on the sheet member and a plurality of massaging elements disposed on the sheet member, the massaging elements operating in accordance with detection results from the gum-condition sensors.

In the disclosed gum massaging device, the gum-condition sensors and the massaging elements may be disposed in a plurality of sections into which the sheet device is divided. The gum massaging device may further include an operation determining unit that, in operation, determines, section by section, an operation of at least one of the massaging elements disposed in each section on the basis of a detection result from at least one of the gum-condition sensors disposed in the section.

In the disclosed gum massaging device, the gum-condition sensor may detect information related to condition specifying a level of a blood circulation of the gum. The massaging element operates in such a manner that the massaging element provides a massage with a higher strength when the level of the blood circulation is lower.

In the disclosed gum massaging device, the operation determining unit may shift a region where each of the massaging elements included in one or more sections provides the massage.

In the disclosed gum massaging device, the sheet member may have such a three-dimensional shape as to be capable of being fitted into an upper or lower oral vestibule.

In the disclosed gum massaging device, the massaging element may stop providing the massage when a degree to which the detection result from the gum-condition sensor has changed from a start of the massage arrives at a predetermined threshold.

In the disclosed gum massaging device, the sheet member may be capable of being attached to the gum and a mucous membrane near a salivary gland. The gum massaging device may further include a salivary-gland massaging element disposed on the sheet member at a position near the salivary gland.

A method for massaging a gum disclosed herein includes operating a gum-condition sensor disposed on a sheet member attachable to the gum to detect information related to a condition of the gum and operating a massaging element, disposed on the sheet member, in accordance with a detection result from the gum-condition sensor.

The disclosure is usable as a gum massaging device and a method for massaging a gum that can effectively improve the gum condition.

What is claimed is:

1. A gum massaging device, comprising:
   a sheet member attachable to a gum, a cross section of the sheet member having a hook-shape;
   gum-condition sensors disposed on the sheet member; and
   massaging elements disposed on the sheet member, the massaging elements being operated in accordance with detection results from the gum-condition sensors,
   wherein the gum-condition sensors and the massaging elements are disposed in sections into which the sheet member is divided,
   wherein the gum massaging device further comprises an operation determining unit that, in operation, determines, section by section, an operation of at least one of the massaging elements disposed in each section on the basis of a detection result from at least one of the gum-condition sensors disposed in the section,
   wherein a first section of the sections corresponds to a first portion of the gum, and a second section of the sections corresponds to a second portion of the gum and a first portion of an inner side of cheeks, the first section touches the second section, a border is provided between the first section and the second section, a cross section of the second section includes a curved portion of the hook-shape, and a cross section of the first section includes a generally straight portion of the hook-shape excluding the curved portion,
   wherein the massaging elements include a first group of massaging elements disposed in the first section and a second group of massaging elements disposed in the second section, the first group of massaging elements includes a first group border massaging element positioned nearest to the border among the first group of massaging elements, and the second group of massaging elements includes a second group border massaging element positioned nearest to the border among the second group of massaging elements,
   wherein the operation includes a first operation and a second operation, the first operation and the second operation are not performed at a same period,
   wherein, under the first operation,
   the first group of massaging elements repeat a first massage, the first massage being provided by activating each of the first group of massaging elements sequentially one time,
   the second group of massaging elements repeat a second massage after a completion of the repeat of the first massage, the second massage being provided by activating each of the second group of massaging elements sequentially one time, and
   wherein, under the second operation,
   the first group of massaging elements excluding the first group border massaging element and the second group of massaging elements excluding the second group border massage element repeat a third massage, the third massage being provided by activating each of the first group of massaging elements excluding the first group border massaging element sequentially one time and then by activating each of the second group of massaging elements excluding the second group border massage element sequentially one time.

2. The gum massaging device according to claim 1,
   wherein each of the gum-condition sensors detects information related to a condition of a portion of the gum that the gum-condition sensor is disposed to, the portion of the gum corresponding to a section included in the sections, and the condition including at least one of a color tone, a tension, a temperature, a blood pressure, a blood flow, and a water content.

3. The gum massaging device according to claim 1,
   wherein each of the gum-condition sensors detects information related to a condition specifying a level of a blood circulation of a portion of the gum that the gum-condition sensor is disposed to, the portion of the gum corresponding to a section included in the sections, and
   each of the massaging elements operates in such a manner that each of the massaging elements provides a massage with a higher strength when the level of the blood circulation is lower.

4. The gum massaging device according to claim 1, wherein the sheet member has such a three-dimensional shape as to be capable of being fitted into an upper or lower oral vestibule.

5. The gum massaging device according to claim 1, wherein each of the massaging elements stops providing the massage when a degree to which the detection result from the gum-condition sensor has changed from a start of the massage arrives at a predetermined threshold.

6. A method for massaging a gum, comprising:
operating massaging elements, disposed on a sheet member attachable to the gum, in accordance with detection results from gum-condition sensors disposed on the sheet member,
providing the sheet member with a cross section having a hook-shape,
wherein the gum-condition sensors and the massaging elements are disposed in sections into which the sheet member is divided,
wherein the gum massaging device further comprises an operation determining unit that, in operation, determines, section by section, an operation of at least one of the massaging elements disposed in each section on the basis of a detection result from at least one of the gum-condition sensors disposed in the section,
wherein a first section of the sections corresponds to a first portion of the gum, and a second section of the sections corresponds to a second portion of the gum and a first portion of an inner side of cheeks, the first section touches the second section, a border is provided between the first section and the second section, a cross section of the second section includes a curved portion of the hook-shape, and a cross section of the first section includes a generally straight portion of the hook-shape excluding the curved portion,
providing the massaging elements to include a first group of massaging elements disposed in the first section and a second group of massaging elements disposed in the second section, the first group of massaging elements includes a first group border massaging element positioned nearest to the border among the first group of massaging elements, and the second group of massaging elements includes a second group border massaging element positioned nearest to the border among the second group of massaging elements,
wherein the operation includes a first operation and a second operation, the first operation and the second operation are not performed at a same period,
wherein, under the first operation,
the first group of massaging elements repeat a first massage, the first massage being provided by activating each of the first group of massaging elements sequentially one time,
the second group of massaging elements repeat a second massage after a completion of the repeat of the first massage, the second massage being provided by activating each of the second group of massaging elements sequentially one time,
wherein, under the second operation,
the first group of massaging elements excluding the first group border massaging element and the second group of massaging elements excluding the second group border massage element repeat a third massage, the third massage being provided by activating each of the first group of massaging elements excluding the first group border massaging element sequentially one time and then by activating each of the second group of massaging elements excluding the second group border massage element sequentially one time.

* * * * *